US012797319B2

(12) United States Patent
Fan et al.

(10) Patent No.: US 12,797,319 B2
(45) Date of Patent: *Nov. 17, 2026

(54) HAIR DYE COMPOSITION

(71) Applicant: The Procter & Gamble Company, Cincinnati, OH (US)

(72) Inventors: Shufen Fan, Singapore (SG); Mei Yi Tee, Singapore (SG); Pei Qi Lim, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/202,331

(22) Filed: May 8, 2025

(65) Prior Publication Data

US 2025/0262138 A1 Aug. 21, 2025

Related U.S. Application Data

(63) Continuation of application No. 18/482,285, filed on Oct. 6, 2023, now Pat. No. 12,329,838.

(Continued)

(51) Int. Cl.

*A61Q 5/10* (2006.01)
*A61K 8/49* (2006.01)
*A61Q 5/06* (2006.01)

(52) U.S. Cl.

CPC ................ *A61K 8/49* (2013.01); *A61Q 5/065* (2013.01); *A61K 2800/438* (2013.01); *A61K 2800/81* (2013.01)

(58) Field of Classification Search

CPC ................ A61K 8/49; A61K 2800/438; A61K 2800/81; A61K 8/498; A61Q 5/065

(Continued)

(56) References Cited

U.S. PATENT DOCUMENTS

| | | | |
|---|---|---|---|
| 5,989,573 | A | 11/1999 | Remy |
| 6,080,415 | A | 6/2000 | Simon |

(Continued)

FOREIGN PATENT DOCUMENTS

| | | | |
|---|---|---|---|
| CN | 2845553 | Y | 12/2006 |
| CN | 102485200 | A | 6/2012 |

(Continued)

OTHER PUBLICATIONS

All Office Actions: U.S. Appl. No. 18/906,341, filed Oct. 4, 2024.

(Continued)

*Primary Examiner* — Eisa B Elhilo
(74) *Attorney, Agent, or Firm* — Abbey A. Lopez

(57) ABSTRACT

A tunable hair dye composition that includes at least two photochoromic dyes, each activatable by activating electromagnetic radiation and deactivatable by deactivating electromagnetic radiation. The composition can be applied to a target skin or hair surface and, when activated, impart a temporary color change to the skin or hair. Prior to activation, the photochromic dye is generally colorless. The intensity or shade of a color imparted by a photochromic dye can be tuned by adjusting the fluence of the activating and/or deactivating electromagnetic radiation. Thus, a wide variety of different hair colors can be obtained from a single hair dye composition containing specific combinations of photochromic dyes.

10 Claims, 4 Drawing Sheets

Related U.S. Application Data

(60) Provisional application No. 63/414,049, filed on Oct. 7, 2022.

(58) Field of Classification Search
USPC .............................................................. 8/405
See application file for complete search history.

(56) References Cited

U.S. PATENT DOCUMENTS

| | | | | |
|---|---|---|---|---|
| 6,123,952 | A * | 9/2000 | Lagrange | A61K 8/49 424/59 |
| 6,190,677 | B1 | 2/2001 | Remy | |
| 6,224,884 | B1 | 5/2001 | Remy | |
| 6,531,118 | B1 | 3/2003 | Gonzalez | |
| 7,022,331 | B2 | 4/2006 | Theisen | |
| 7,530,358 | B2 | 5/2009 | Elliott | |
| 7,550,136 | B2 | 6/2009 | Warner | |
| 7,621,966 | B2 | 11/2009 | Brun | |
| 7,682,405 | B2 | 3/2010 | Brun | |
| 7,776,316 | B2 | 8/2010 | Kolodziej | |
| 8,035,061 | B2 | 10/2011 | Jung | |
| 9,827,311 | B2 | 11/2017 | Laboureau | |
| 9,949,544 | B2 | 4/2018 | Samain | |
| 10,702,044 | B2 | 7/2020 | Streeter | |
| 10,994,156 | B2 | 5/2021 | Shami | |
| 11,872,295 | B2 | 1/2024 | Moore | |
| 12,329,838 | B1 | 6/2025 | Fan et al. | |
| 2002/0122780 | A1 | 9/2002 | Mcmanus | |
| 2003/0118531 | A1 | 6/2003 | Kolodziej et al. | |
| 2005/0268405 | A1 | 12/2005 | Brun | |
| 2005/0273947 | A1 | 12/2005 | Brun | |
| 2005/0276767 | A1 | 12/2005 | Blin | |
| 2006/0088488 | A1 | 4/2006 | Brun | |
| 2007/0053856 | A1 | 3/2007 | Ribi | |
| 2007/0071414 | A1 | 3/2007 | Vena et al. | |
| 2007/0248560 | A1 | 10/2007 | Livoreil | |
| 2007/0261179 | A1 | 11/2007 | Dorkel et al. | |
| 2008/0102046 | A1 | 5/2008 | Thevenet | |
| 2008/0117785 | A1 | 5/2008 | Ito | |
| 2009/0145452 | A1 | 6/2009 | Anderson | |
| 2010/0043819 | A1 | 2/2010 | Feng | |
| 2010/0139682 | A1 | 6/2010 | Edgar et al. | |
| 2010/0215599 | A1 | 8/2010 | Giron | |
| 2010/0252061 | A1 | 10/2010 | Samain | |
| 2012/0017929 | A1* | 1/2012 | Samain | A61K 8/69 132/288 |
| 2012/0024308 | A1 | 2/2012 | Giron | |
| 2015/0164196 | A1 | 6/2015 | Teboul | |
| 2016/0250132 | A1 | 9/2016 | Sutton | |
| 2017/0013943 | A1 | 1/2017 | Uchida | |
| 2019/0133284 | A1 | 5/2019 | Ha | |
| 2020/0315932 | A1 | 10/2020 | Desai | |
| 2021/0308020 | A1 | 10/2021 | Bowker et al. | |
| 2022/0048303 | A1 | 2/2022 | Koibuchi | |
| 2022/0054395 | A1 | 2/2022 | Nowottny | |
| 2022/0062156 | A1 | 3/2022 | Neuba | |
| 2022/0323335 | A1 | 10/2022 | Kruck | |
| 2022/0354769 | A1 | 11/2022 | Kruck | |
| 2022/0354770 | A1 | 11/2022 | Kruck | |
| 2022/0354771 | A1 | 11/2022 | Kruck | |
| 2022/0370330 | A1 | 11/2022 | Kruck | |
| 2022/0370332 | A1 | 11/2022 | Kruck | |
| 2022/0378686 | A1 | 12/2022 | Kruck | |
| 2022/0378687 | A1 | 12/2022 | Kruck | |
| 2022/0387292 | A1 | 12/2022 | Kruck | |
| 2023/0181429 | A1 | 6/2023 | Moore et al. | |
| 2025/0114285 | A1 | 4/2025 | Fan et al. | |
| 2025/0114289 | A1 | 4/2025 | Fan et al. | |

FOREIGN PATENT DOCUMENTS

| | | | |
|---|---|---|---|
| CN | 102631294 | A | 8/2012 |
| CN | 102641215 | A | 8/2012 |
| CN | 202915316 | U | 5/2013 |
| CN | 105232421 | A | 1/2016 |
| CN | 110101599 | A | 8/2019 |
| CN | 114277585 | A | 4/2022 |
| EP | 0847751 | B1 | 4/2002 |
| FR | 2845895 | A1 | 4/2004 |
| FR | 2845898 | A1 | 4/2004 |
| FR | 2838960 | B1 | 6/2006 |
| FR | 2845910 | B1 | 6/2007 |
| FR | 2899795 | A1 | 10/2007 |
| FR | 2918667 | A1 | 1/2009 |
| FR | 2928267 | A1 | 9/2009 |
| FR | 2942401 | A1 | 8/2010 |
| FR | 2939655 | B1 | 2/2011 |
| FR | 2953397 | B1 | 1/2012 |
| FR | 2994652 | A1 | 2/2014 |
| GB | 1227784 | A | 4/1971 |
| JP | 2007063433 | A | 3/2007 |
| JP | 4575789 | B2 | 8/2010 |
| JP | 4804573 | B2 | 8/2011 |
| JP | 4920192 | B2 | 2/2012 |
| JP | 2012055370 | A | 3/2012 |
| JP | 2020100710 | A | 7/2020 |
| JP | 7159924 | B2 | 10/2022 |
| KR | 20020072519 | A | 9/2002 |
| KR | 20060092511 | A | 8/2006 |
| KR | 20150050183 | A | 5/2015 |
| KR | 102157736 | B1 | 9/2020 |
| TW | M581912 | U | 8/2019 |
| TW | 202011934 | A | 4/2020 |
| TW | 202011935 | A | 4/2020 |
| WO | 200148092 | A2 | 7/2001 |
| WO | 2012023116 | A1 | 2/2012 |
| WO | 2013041744 | A1 | 3/2013 |
| WO | 2017180898 | A1 | 10/2017 |
| WO | 2020030818 | A1 | 2/2020 |
| WO | 2020074699 | A1 | 4/2020 |
| WO | 2020101139 | A1 | 5/2020 |
| WO | 2020126137 | A1 | 6/2020 |
| WO | 2020260659 | A1 | 12/2020 |
| WO | 2021058206 | A1 | 4/2021 |
| WO | 2021099510 | A1 | 5/2021 |

OTHER PUBLICATIONS

All Office Actions: U.S. Appl. No. 18/482,270, filed Oct. 6, 2023.

All Office Actions; U.S. Appl. No. 18/906,344, filed Oct. 4, 2024.

All Office Actions; U.S. Appl. No. 18/482,285, filed Oct. 6, 2023.

Andrew D. Towns, "Industrial Photochromism", Applied Photochemistry, URL: https://link.springer.com/chapter/10.1007/978-3-319-31671-0_5; 2016, 21 pages.

Dushanthi S. et al, "Systematic variation of thiophene substituents in photochromic spiropyrans", Photochemical & Photobiological Sciences, URL: https://link.springer.com/article/10.1039/c7pp00057j, 2017, 07 pages.

György Szalóki et al, "Properties and Applications of Indolinooxazolidines as Photo-, Electro-, and Acidochromic Units", URL: https://link.springer.com/chapter/10.1007/978-4-431-56544-4_3; 2017, 17 pages.

Hazem Amarne et al, "Photochromic N, C-chelate 4-coordinate organoboron compounds", Ottawa : Library and Archives Canada= Bibliothèque et Archives Canada, URL: https://scholar.google.com/scholar?hl=en&as_sdt=0%2C5&q=%22PHOTOCHROMIC+N%2CC-CHELATE+4-COORDINATE+ORGANOBORON+COMPOUND%22&btnG=, 2003, 03 pages.

Marinella Ferrara et al, "Materials that Change Color" SpringerLink, URL: https://link.springer.com/chapter/10.1007/978-3-319-00290-3_2; 2014, 23 pages.

Matthew L. Davies et al, "Photochemical Materials: Absorbers, Emitters, Displays, Sensitisers, Acceptors, Traps and Photochromics", Applied Photochemistry, URL: https://link.springer.com/chapter/10.1007/978-90-481-3830-2_4, 2013, 35 pages.

Rosario Pardo et al, "Photostability of a photochromic naphthopyran dye in different sol-gel prepared ormosil coatings", Journal of Sol-Gel Science and Technology, vol. 40, URL: https://link.springer.com/article/10.1007/s10971-006-8774-z, 2006, 8 pages.

(56) References Cited

OTHER PUBLICATIONS

Unpublished U.S. Appl. No. 18/482,270, filed Oct. 6, 2023, to Fan Shufen et al.

* cited by examiner

R = H, $CH_3$, or tert-butyl

R = $CH_3$, $CH_2CH_3$, n-propyl, n-butyl, n-pentyl, n-hexyl, n-heptyl, or n-octyl R = Cl, $OCH_3$, or $CF_3$

HAIR DYE COMPOSITION

FIELD

The present disclosure generally relates to a hair dye composition that enables a user to tunably change the color of their hair by applying a suitable energy source to the hair dye composition. More specifically, the present disclosure relates to a hair dye composition that contains two or more photochromic dyes specifically tailored to provide multiple hair color changes upon the application of electromagnetic radiation.

BACKGROUND

Altering the color of human hair has long been used to cosmetically adapt a person's appearance to the fashion and style trends of the day. Conventional hair coloring techniques typically involve the application of a temporary, semi-permanent, demi-permanent or permanent chemical dye (oxidative or non-oxidative) to the hair to achieve a color change. Conventional hair dyes can provide a wide variety of hair color changes, hair lightening effects and hair darkening effects. However, conventional hair dyes are limited to providing a single hair color change. Additional hair color changes require application of a different hair dye composition. If a user desires a return to their natural hair color, then they must wait for the dye to be washed out or, in the case of permanent dyes, for the hair to grow out and the dyed portion cut off. Thus, the use of conventional hair dyes can be inconvenient and time consuming.

To address some of the drawbacks of conventional hair dyes, photochromic dyes have been examined for color change options and flexibility. For example, FR 1,604,929 describes a hair composition that contains compounds such as nitrobenzylpyridines, thiosemicarbazones or spiropyran derivatives. When these compounds are exposed to electromagnetic radiation ("EMR") of a particular wavelength (e.g., ultraviolet radiation with a wavelength of 100-400 nm), the dye compound undergoes a conformational change that alters the color of the dye. When the EMR is removed, the molecule reverts to its previous conformation and color. Compositions that contain thes photochromic dyes disclosed in FR 1,604,929 may provide additional flexibility and convenience for changing hair or skin color, but it would be desirable to provide a hair coloring composition that does not depend on the presence or absence of a particular wavelength of EMR to maintain the desired color change.

In another example, U.S. Pat. No. 6,123,952 discloses a cosmetic composition that contains a thermally-irreversible, photochromic coloring agent, preferably selected from diarylethene compounds and fulgide compounds. According to U.S. Pat. No. 6,123,952, after the composition is applied to a bodily surface, it is exposed to EMR of a particular wavelength (e.g., ultraviolet radiation), which causes the photochromic dye to change color. When the UVR is removed, the photochromic dye retains its color. And when the dye is exposed to a different EMR wavelength, the dye returns to its original color. While the hair dye compositions of U.S. Pat. No. 6,123,952 may provide additional flexibility and convenience for coloring hair or skin, these compositions are still limited to a single hair color change (i.e., coloring and de-coloring).

Another disadvantage of photochromic dyes, such as those disclosed in U.S. Pat. No. 6,123,952, is the lack of suitable solvents for use in hair dye compositions. For example, p-type photochromic dyes such as diarylethenes are readily dissolved in organic solvents such as toluene or formaldehyde. However, these types of organic solvents are generally not suitable for cosmetic use on skin and hair. While U.S. Pat. No. 6,123,952 discloses solvents that may be suitable for lotions and creams, these solvents may not be suitable for hair dye compositions.

Accordingly, it would be desirable to provide a photochromic hair dye composition that enables a user to conveniently change their hair color multiple times with a single hair dye composition. It would also be desirable to provide a photochromic hair dye composition that contains a solvent suitable for use on human skin and hair.

SUMMARY

Disclosed herein is a hair dye composition comprising a first photochoromic dye activatable by a first activating electromagnetic radiation (EMR) and deactivatable by a first deactivating EMR; a second photochromic dye activatable by a second activating EMR and deactivatable by a second deactivating EMR, wherein the first and second deactivating EMR are different; and a solvent. A lso disclosed is a method of tunably coloring hair comprising identifying a target portion of hair having a first hair color where a color change is desired; applying the hair dye composition of claim 1 to the target portion of hair; activating at least one of the first and second photochromic dyes by irradiating the hair dye composition with EMR having a wavelength of 250 nm to 395 nm to yield a second hair color; and deactivating at least one of the first and second photochromic dyes by irradiating the hair with EMR having a wavelength of 400-700 nm to yield a third hair color.

DETAILED DESCRIPTION

Figure 1A:
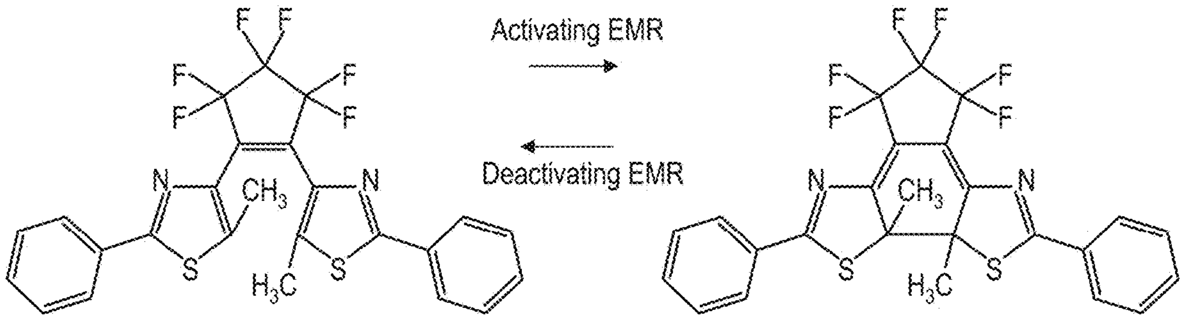
FIGS. 1A, 1B, and 1C are examples of photochromic dyes.

The use of photochromic compounds for cosmetic applications is known. However, previous attempts at commercializing photochromic hair dye compositions have failed, as evidenced by the lack of such products in the market. Previously described compositions and methods involving photochromic dyes require continuous application of EMR only enable a single hair color change. The hair dye compositions disclosed herein overcome the draw backs of previous hair dye composition by exploiting combinations of photochromic dye compounds that enable multiple hair color changes with the use of a single hair dye composition. In some aspects, the novel hair dye compositions herein enable a user to tune the color of their hair by applying EMR of varying wavelength and/or fluence.

It has also been discovered that certain cosmetically safe (i.e., GRAS) solvents are effective for use with certain p-type photochromic dyes. P-type photochromic dyes tend to exhibit poor solubility in solvents commonly used in conventional hair dye compositions (e.g., water, ammonia andamines). Toluene and formaldehyde are known to be good solvents for p-type photochromic compounds, but they are generally not suitable for use in products that are applied to human skin and hair. Certain alcohols and esters may be suitable solvents for certain photochromic dyes, for example as disclosed in U.S. Pat. No. 6,123,952, but may not be suitable for all photochromic dyes and may be perceived by consumers as being harsh on their hair. It has not been discovered that photochromic hair dye compositions can be formulated with consumer preferred solvents such as botanical oils, some of which were previously unappreciated for this use.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

All ingredient percentages described herein are by weight of the composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. Unless otherwise indicated, all measurements are understood to be made at approximately 25 °C and at ambient conditions, where "ambient conditions" means conditions under about 1 atmosphere of pressure and at about 50% relative humidity. All numeric ranges are inclusive of narrower ranges not explicitly delineated within these ranges, and delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"About" modifies a particular value by referring to a range of plus or minus 20% or less of the stated value (e.g., plus or minus 15% or less, 10% or less, or even 5% or less).

"Activate" and variations thereof, when referring to a photochromic dye or a composition comprising a photochromic dye, means causing the photochromic dye and/or composition to change color by exposing it to electromagnetic radiation ("EMR") of a particular wavelength or changing the temperature of the dye.

"Color" refers to visibly perceived light of a particular wavelength, generally between 400 nm and 700 nm. Color can be characterized in terms of Hue, Saturation, and Lightness, and can be measured using conventional methods, for example, with a spectrophotometer or colorimeter.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the U.S. Food and Drug Administration.

"Deactivate" and variations thereof, when referring to a photochromic dye or a composition comprising a photochromic dye, means causing the photochromic dye and/or composition to revert back to substantially the same color it was prior to activation by exposing the dye to EMR of a particular wavelength, removing activating EMR or changing the temperature of the dye.

"Different colors" and variations thereof mean colors that have a different Hue, Saturation and/or Lightness value relative to one another. In some aspects, different colors can be characterized by having a $\Delta E$ of greater than 1, relative to one another, according to the Color Measurement method.

"Fluence" means the time-integrated flux of EMR (i.e., activating EMR and deactivating EMR) on an irradiated surface. Fluence can be readily determined by those skilled in the art.

"Suitable for application to human hair" means that the composition or components thereof, are acceptable for use in contact with human hair and the scalp and skin without undue toxicity, incompatibility, instability, and the like.

"Substantially free of" means a composition or ingredient contains less than 3% (e.g., less than 2%, 1% or even less than 0.5%) of a subject material, by weight of the composition or ingredient. "Free of" means 0% of a subject material is present in the composition or ingredient.

"Tunable" means that the hair color change provided by the photochromic hair dye compositions herein can be adjusted to a desired color. The hair color change may be tuned, for example, by changing: the activating/deactivating time, the strength of the EMR source, the concentration or ratio of photochromic dyes and/or the activating/deactivating technique (e.g., how close the EMR source is to the hair or selectively exposing target portions of hair to the EMR source).

"Visible color change" and variations thereof mean a color change that results in a $\Delta E$ of more than 1 (e.g., 2, 3, 5, 10, 20 or more). $\Delta E$ can be determined according to the Color Measurement method described in more detail below.

Hair Dye Composition

The cosmetic hair dye compositions herein are suitable for application to a keratinous surface such as hair or skin and provide a convenient way for a user to tune the color of their hair between at least 3 visibly different colors, which are the original hair color, a first new color, and a second new color. The tunable hair dye compositions herein include at least two different photochromic dyes, a cosmetically acceptable solvent and a carrier, as well as other optional ingredients commonly found in hair care compositions such as hair dyes, shampoos, conditioners, hair styling products and the like. The photochromic dyes may each be present in the hair dye composition at 0.01% to 25% (e.g., 0.05% to 20%, 0.1% to 10%, 0.5% to 5%, or even 1% to 3%). The composition also includes a suitable solvent to ensure the dyes are suitably dispersed in the carrier. The solvent may be present at 1% to 99.99% (e.g., 2% to 90%, 3% to 80%, 4% to 70%, or even 5% to 50%). The pH of the hair dye compositions herein may be between 2 and 10 (e.g., 3, 4, 5, 6, 7, 8 or 9). The hair dye compositions herein may be provided in various product forms such as solutions, suspensions, shampoos, conditioners, lotions, creams, gels, sticks, sprays, aerosols, ointments, solid bars, pastes, foams, mousses, hydrogels, and the like. The composition form may follow from the particular dermatologically acceptable carrier chosen.

In some embodiments, the photochromic dyes are included in the hair dye composition at a ratio of first dye to second dye of 1:50 to 50:1 (e.g., 1:30, 1:20, 1:10, 1:5, 1:3, 1:2, 1:1, 2:1, 3:1, 5:1, 10:1, 20:1, or 30:1), depending on the desired hair color change. Of course, one or more additional photochromic dyes may also be included at a suitable ratio to the first and/or second dye. It is to be appreciated that the ratio of the photochromic dyes in the composition can be important for providing the desired hair color change to users who have different hair colors. For example, to provide the same or similar color of hair to a user with blond hair and a user with black hair, it may be necessary for the ratio of photochromic dyes in the hair dye composition to be different.

Hair color can be classified on a scale of 1 to 10 based on well-known hair color charts such as the one below.

| 1 | 2 | 3 | 4 | 5 | 6 | 7 | 8 | 9 | 10 |
|---|---|---|---|---|---|---|---|---|---|
| Lightest Blonde | Medium Blonde | Dark Blonde | Lightest Brown | Medium-light Brown | Medium Brown | Dark Brown | Darkest Brown | Black | Darkest Black |

The hair color values shown in the chart can readily be correlated to red, green, and blue color values based on the RGB color models, for example, as described in US 2021/0308020. Additionally or alternatively, the hair color values can be correlated to other known color values/models such as: cyan, magenta, yellow, black (CMYK) color values; L*a*b* color values, as defined by the International Commission on Illumination (CIE Lab); or Hue, Saturation, and Lightness (HSL) color values. By tailoring the type and amount of dye in the composition based on the color interactions of known color models, it is possible to provide a user with a more predictable hair color and a wider range of tunable color options.

Providing temporary color effects to medium or darker colored hair is known to be problematic. Conventional hair coloring systems may resort to pre-treating darker colored hair to lighten the color of the hair, of the hair, sometimes referred to as bleaching and then applying a desired final color. However, bleaching is known to be harmful to hair. By tailoring the combination of photochromic dyes to the user's hair color, the hair dye compositions described herein can provide a desired visible hair color change without the need to lighten or otherwise pre-treat the hair.

The hair dye compositions herein provide an excellent aesthetic appearance to hair. In particular, the hair dye compositions herein can provide excellent Hue, Saturation, Lightness, and/or Gloss to the hair. "Hue" refers to the color obtained and corresponds to value ranging from 0° to 360° (e.g., 0° (red), 30° (orange), 60° (yellow), 90°, 120° (green), 150°, 180° (cyan), 210°, 240° (blue), 270° (violet), 300° (magenta), or) 330°. "Saturation" is the intensity of the color and has a value ranging from 0% (gray) to 100% (pure color). "Lightness" is the amount of white or black mixed with the color to provide various tints and shades. The Lightness value can be 0% (black) to 100% (white). Gloss is the amount of light reflecting from a surface which gives the effect of shine and can range from 1 to 100, where a lower value indicates lower gloss/higher matte. HSL values can be measured using a spectrophotometer according to the Color Measurement method described in more detail below. Gloss can be measured concurrently with HSL, for example, by setting the SCI/SCE mode on a suitable spectrophotometer to include a specular component (SCI mode) whereby reflected light from a surface is quantified as the Gloss value. Additionally or alternatively, L*a*b* colors values can be measured with a suitable spectrophotometer and converted to HSL color values.

In some aspects, the hair dye compositions herein may be provided to a user in a package that enables the user to activate and/or deactivate the hair dye composition in the package, for example, by irradiating the hair dye composition with EMR through a transparent portion of the package. The hair dye composition, when activated and/or deactivated in its package, may have the same or different color properties from what it has when applied to hair and then activated and/or deactivated. In some instances, the hair dye composition may be exposed to EMR in its package to partially activate and/or deactivate it, and then applied to the hair and exposed to additional EMR to further activate and/or deactivate the hair dye composition.

The hair dye compositions herein enable a user to conveniently change the visible color of their hair to a variety of different colors with a single hair dye composition. The hair dye composition may be tailored to deliver a visible color change based on the fluence of the activating EMR, the wavelength of the activating EMR. the fluence of the deactivating EMR, the wavelength of the deactivating EMR, the activation time of the photochromic dye, and/or the deactivation time of the photochromic dye. In some aspects, the hair dye compositions herein may provide long lasting color change (e.g., more than 2 hours, 4 hours, 8 hours, 12 hours, 18 hours, or even 24 hours or more) upon activation and/or deactivation.

The color of the photochromic dyes in the hair dye composition, when activated, are not particularly limited and may be any color, as desired. In some instances, it may be desirable for the activated dye color to be selected from cyan, magenta, yellow, and combinations thereof to take advantage of CMYK printing principles to provide a wide range of different colors. Cyan may be characterized as having an HSL value of 300°, 100% and 50%. Magenta may be characterized as having an HSL value of 180°, 100% and 50%. Yellow may be characterized as having an HSL value of 60°, 100% and 50%. In some instances, a color that has a Hue value within 3°, a Saturation value within 10%, and a Lightness value within 10% of the target value for a particular color may be considered that color. For example, a color with an HSL value of 178°, 95%, 45% may be considered Cyan.

Photochromic Dye

Photochromic dyes are generally recognized as dyes that undergo a reversible color change when exposed to EMR of a particular wavelength and fluence ("activating EMR"). Photochromic dyes are classified into two types, p-type and t-type. When a photochromic dye is exposed to an activating and/or deactivating EMR it undergoes a molecular transformation between isomers of the photochromic dye molecule.

The compositions herein include a p-type photochromic dye. The p-type photochromic dyes suitable for use herein can be activated by an activating EMR having a wavelength of 250 nm to 395 nm (e.g., 260 nm to 380 nm or 270 nm to 370 nm) and a fluence of 1 mj/cm$^2$ to 50 J/cm$^2$. In some aspects, the hair dye compositions include two or more different photochromic dyes. For example, the hair dye composition may include two or more p-type photochromic dyes, a p-type photochromic dyes and a t-type photochromic dyes, or a combination of photochromic dyes and a non-photochromic hair dye.

P-type photochromic dyes are thermally irreversible, but photochemically reversible. In other words, a p-type photochromic dye will change color when irradiated with activating EMR but will generally not revert back to its original color when the activating EMR is removed or when the temperature of the dye changes. A p-type photochromic dye is deactivated by exposing the dye to deactivating EMR, which has a different wavelength from the activating EMR. In some embodiments, the deactivating EMR has a wavelength of 400 to 700 nm (e.g., 425 nm to 650 nm) and a fluence of 1 mj/cm$^2$ to 50 J/cm$^2$. The photochromic dyes suitable for use herein may have an activation and/or deactivation time of less than 1 second up to 10 minutes (e.g., 0.001 seconds to 5 minutes, 0.01 second to 3 minutes, 0.1 second to 2 minutes seconds, 0.5 second to 90 seconds, or even 10 seconds to 60 seconds). Relatively shorter activation and/or deactivation times may be more convenient to a user, and therefore preferred.

In some instances, the p-type photochromic dyes used herein include those belonging to the diarylethene ("DAE") family and/or fulgide family. Some non-limiting examples of diarylethene and fulgide photochromic dyes are described in U.S. Pat. No. 6,123,952 and US20120017929. Some particularly suitable examples of P-type photochromic dyes for use herein include DAE-0001 (cyan), DAE-0012 (magenta), DAE-0068 (yellow) from Yamada Chemical Company.

Figure 1B:
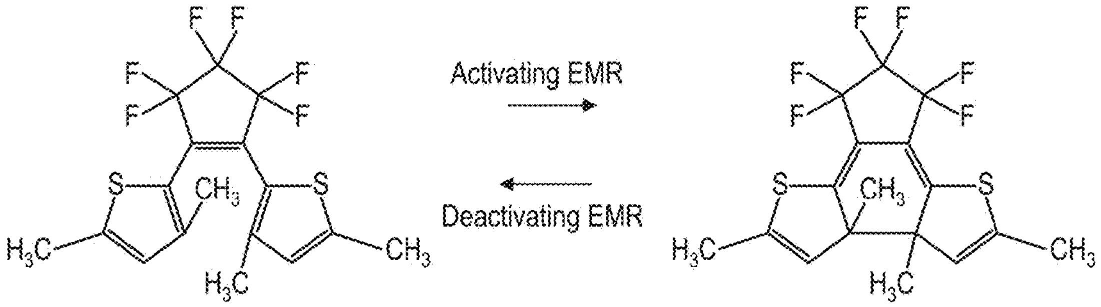
Figure 1C:
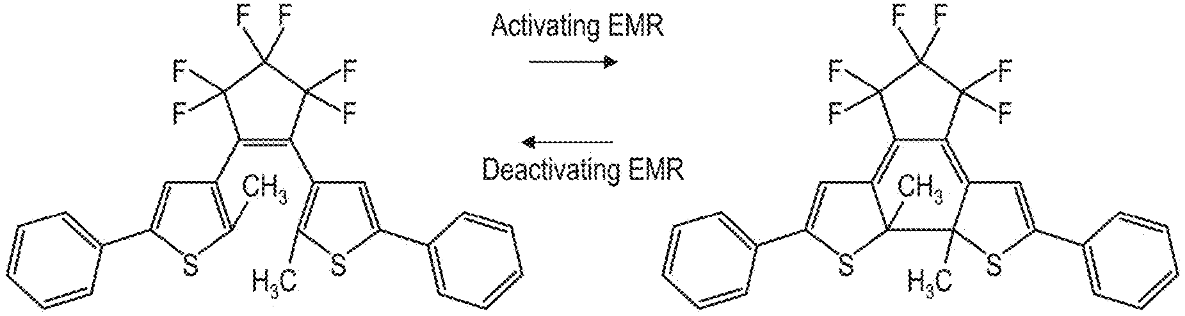
Figure 2A:
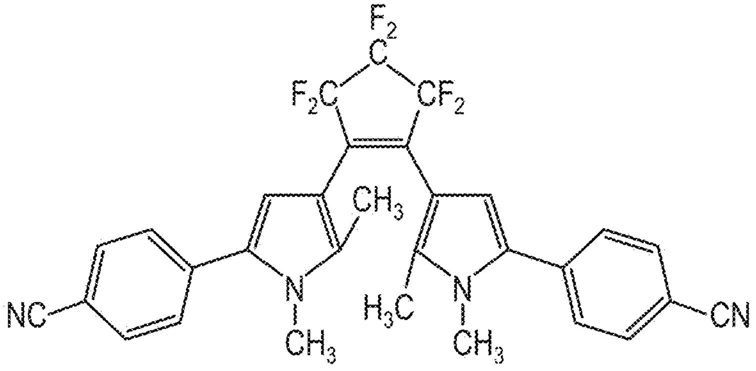
FIGS. 2A, 2B, 2C, 2D, 2E, 2F, and 2G are examples of photochromic dyes.
Figure 2B:
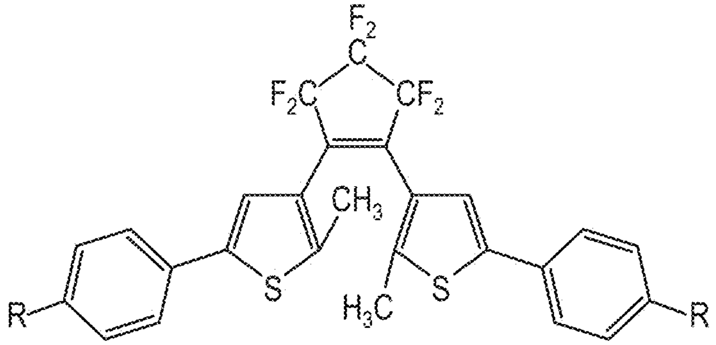
Figure 2C:
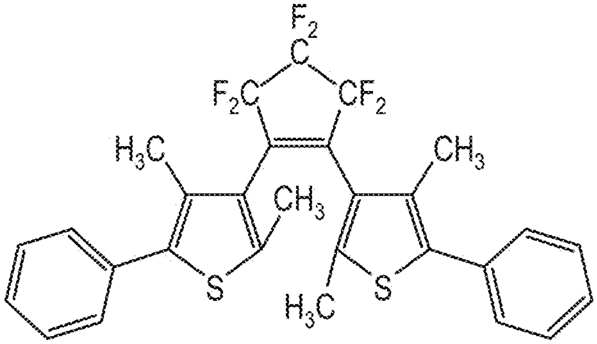
Figure 2D:
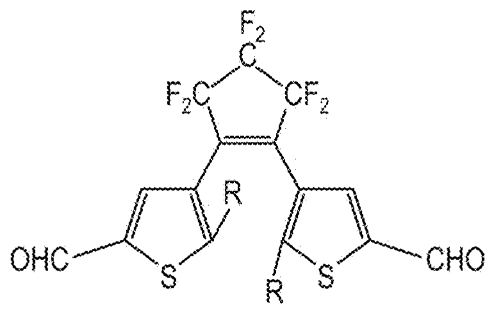
Figure 2E:
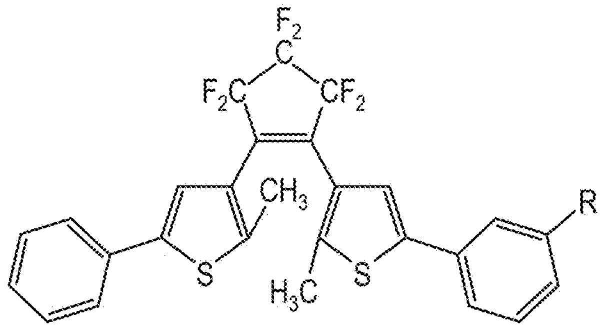
Figure 2F:
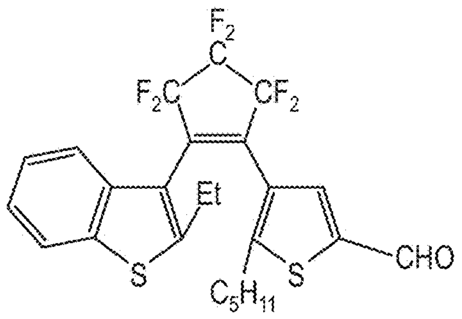
Figure 2G:
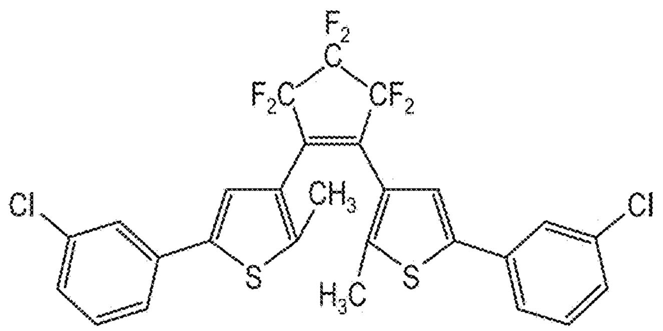

FIGS. 1A, 1B, and 1C depict the chemical structures of diarylethene photochromic dyes. FIG. 1A depicts 4,4'-(perfluorocyclopent-1-ene-1,2-diyl)bis(5-methyl-2-phenylthiazole), which is a P-type photochromic dye that changes from clear to magenta when exposed to a suitable activation energy. FIG. 1B depicts 5,5'-(perfluorocyclopent-1-ene-1,2-diyl)bis(2,4-dimethylthiophene), which is a p-type photochromic dye that changes from clear to yellow when exposed to a suitable activation energy. FIG. 1C depicts 3,3'-(perfluorocyclopent-1-ene-1,2-diyl)bis(2-methyl-5-phenylthiophene), which is a p-type photochromic dye that changes from clear to cyan when exposed to a suitable activating energy. In FIGS. 1A, 1B and 1C, the structures on the left-hand side illustrate the unactivated state of the dye, and the structures on the right-hand side illustrate the activated state of the dye. As illustrated in the figures, the activated dyes have a closed ring structure and the unactivated dye have an open ring structure. The wavelength of the activating EMR for the photochromic dyes illustrated in FIGS. 1A, 1B, and 1C can range from 250 nm to 395 nm, and the wavelength of the deactivating EMR can range from 400 nm to 700 nm, depending on the dye. The fluence of the activating and deactivating EMR of the photochromic dyes can be 1 mj/cm$^2$ to 50 J/cm$^2$.

FIGS. 2A to 2G depict additional examples of blue photochromic dyes (i.e., dyes that generally appear blue to the human eye when activated by an activating EMR).

In some embodiments, the hair dye compositions herein may include one or more t-type photochromic dyes. T-type photochromic dyes are thermally reversible, which generally means they will revert back to their original color once the activating EMR is removed. T-type photochromic dyes include azobenzene and spiropyran compounds. Some non-limiting examples of T-type photochromic dyes can be found in U.S. Pat. Nos. 5,581,090, 5,730,961, and FR 1604929.

Carrier

The hair dye composition herein includes 1%-95% of a cosmetically acceptable carrier. The carrier will typically be liquid, but embodiments in which the carrier is solid or semi-solid (e.g., gel) are also contemplated herein. The carrier may include polar and/or non-polar materials and may be in the form of a single phase (e.g., solution or dispersion) or multiple phases (e.g., an oil-in-water or water-in-oil emulsion). In some embodiments, the carrier includes a solvent in which the photochromic hair dye compounds are soluble. The solvent may make up some or all of the carrier (e.g., 5% to 100%). In some embodiments, the photochromic dye has a solubility of 1 mg/L to 1.5 kg/L in the solvent. Some non-limiting examples of solvents that may be suitable for dissolving DAE photochromic dyes include emulsifiers (e.g., Tween® 20, Tween® 40, Tween® 60, and Tween® 80 brand polysorbate and Span® 20, Span® 40, Span® 60 and Span® 80 brand sorbitan laurate), fatty acids (e.g., steric acid, oleic acid, and palmitic acid), fatty alcohols (e.g., cetyl alcohol, lauryl alcohol, stearyl alcohol, oleyl alcohol, and octyldodecanol), fatty esters (e.g., caprylic/capric triglyceride, isopropyl palmitate, and isopropyl myristate), silicones (e.g., cyclopentasiloxane, cyclohexasiloxane, dimethicone, and methicone) and botanical oils (e.g., wheatgerm oil, beauty-leaf oil, sesame oil, macadamia oil, grapeseed oil, rapeseed oil, coconut oil, groundnut oil, palm oil, castor oil, jojoba oil, olive oil or cereal germ oil, cedarleaf oil, turpentine oil, and *eucalyptus* oil) and combinations of these. Botanical oils may be particularly suitable because they can be naturally and/or sustainably sourced and are generally perceived by consumers as being better for their body.

Optional Ingredients.

The hair dye compositions herein may include other optional ingredients commonly found in hair dye compositions and/or other cosmetic hair and/or skin care compositions. These additional ingredients may be present at 0.5% to 95%. Some non-limiting examples of optional ingredients can be found in U.S. Pat. No. 7,056,351 and US2002/0053110 and may include non-photochromic hair dyes, stabilizing agents (e.g., UV stabilizing agents), binding agents, deposition aids, organic acids, surfactants, hair or skin conditioning agents, anti-dandruff actives, fungicides, alkyl ethoxylate hydrocarbons, silicone compounds, cationic polymers, proteins, amino acids, preservatives, moisturizing agents, viscosity modifiers, emulsifiers, pH modifiers, buffering agents, chelants, and combinations of these.

Method of Making

In some embodiments, the hair dye compositions may be made using conventional methods of making such compositions. In some embodiments, it may be desirable to combine the photochromic dyes and a solvent into a premix, which is then added to the carrier and/or other ingredients in the hair dye composition.

Method of Use

The hair dye compositions herein can be applied to a target portion of hair where a color change is desired. The target portion of hair may be wet or dry and may applied by a hair professional or at home. In one example, it may be desirable to wash the hair, but not condition it, and then dry the hair before applying the hair dye composition. In this example, after applying the hair dye composition, the hair dye composition is allowed to remain on the hair, optionally covered (e.g., with a shower cap or the like), for at least 10 minutes (e.g., 15, 20, 25, 30, or even up to 60 minutes) before rinsing the hair with water. The hair may then be irradiated with an activating EMR, such as one of the EMR types described herein, followed by irradiation with a second (or more) activating EMR and/or one or more deactivating EMR, such as one of the deactivating EMR described herein.

In some instances, it may be desirable to activate and/or deactivate the photochromic dye in the hair dye composition prior to applying it to hair. For example, a dye composition comprising two or more photochromic dyes may be placed in a transparent or translucent container and exposed to an activating EMR to change at least one of the dyes to a different color. The activated or partially activated hair dye composition may then be applied to the hair. Additionally or alternatively, the hair dye composition may be exposed to a second activating EMR and/or first deactivating EMR to provide a second color and prior to application to the hair. Further, the activated hair dye composition may be exposed to an additional activating EMR or deactivating EMR after application to hair. This process may be repeated as needed to achieve a desired hair color.

Hair Dye Product

The hair dye compositions herein may be placed in a primary and, optionally, a secondary package and displayed in a retail environment for sale. The material(s) used to make the primary and/or secondary packaging is not particularly limited and can include any suitable material known for use in hair dye packaging. In some aspects, it may be desirable to use sustainably sourced and/or recyclable materials. The package may include indicia that communicate to a consumer that the hair dye product is a tunable hair dye product. For example, the package may depict hair with its natural color and the hair with two or more other colors provided by the hair dye composition. In some aspects, the packaging may include indicia, for example as illustrated in FIG. 3 or FIG. 4, that show a spectrum of hair colors provided the hair dye composition as a function of EMR exposure time and/or fluence.

Figure 3:
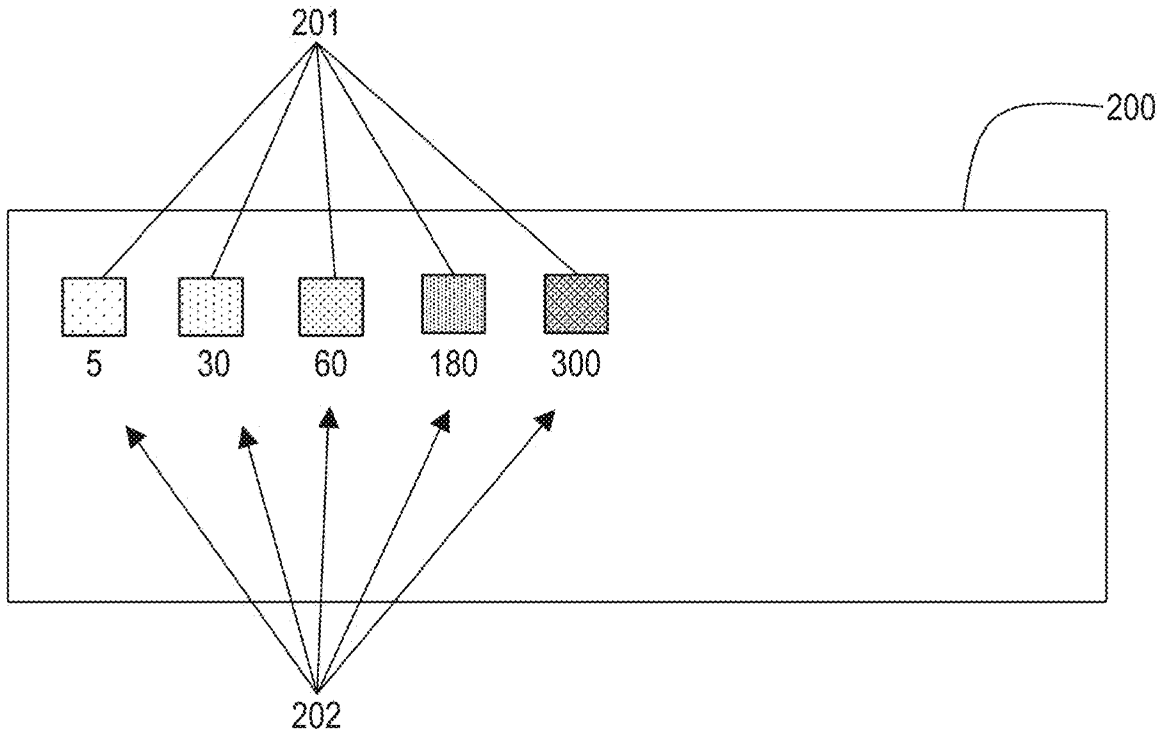
FIG. 3 is an example of package for a hair dye composition containing a photochromic dye.

FIG. 3 illustrates an example of a secondary package 200 in the form of a box. The secondary package 200 is configured to house a primary package containing a hair dye composition. The primary package may be in the form of a bottle, jar, vial or other package suitable for containing a hair dye composition. In some aspects, a primary package and/or hair dye composition may be visible through a window in the secondary package 200. In some aspects, it may be desirable to inhibit or prevent EMR from reaching the hair dye composition, for example, by configuring the primary and/or secondary packages to block EMR that can activate and/or deactivate a hair dye composition contained in the primary packaging (e.g., EMR having a wavelength of 200 to 700 nm, 250 to 700 nm, 400 to 700 nm, or 280 to 400 nm).

The secondary package 200 may include indicia that communicate the tunable aspect of the hair dye composition. In the example depicted in FIG. 3, the indicia include a series of colored squares 201. Each square 201 is a different color and corresponds to the color of the dye after exposure to activating EMR or deactivating EMR for a particular duration. The indicia in FIG. 3 also include numbers 202 to indicate the duration of EMR exposure that results in the color in each square (i.e., 5 seconds, 10 seconds, 30 seconds, 60 seconds, and 120 seconds).

Figure 4:
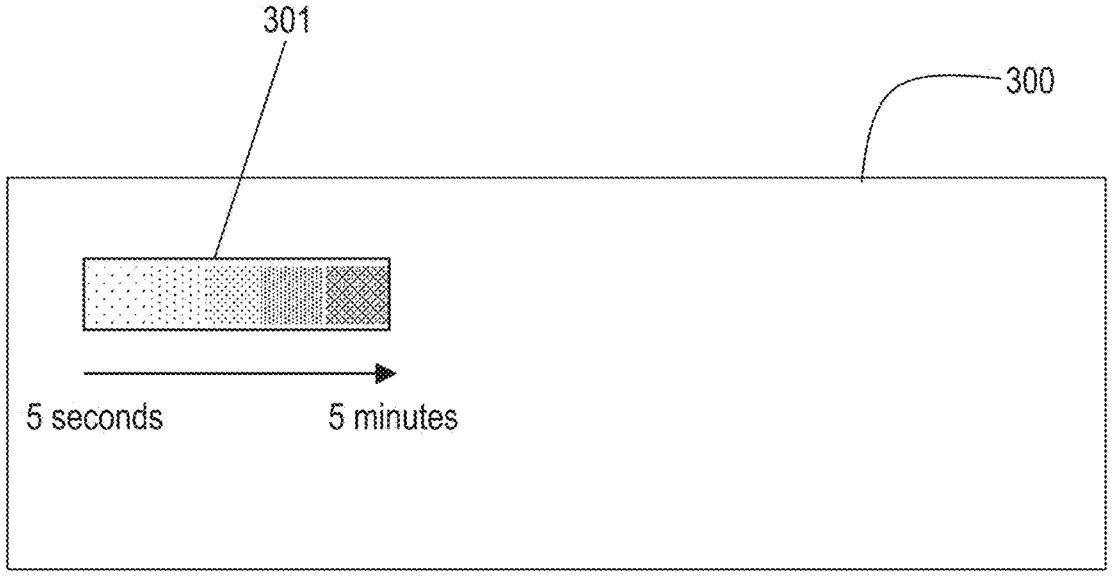
FIG. 4 is an example of package for a hair dye composition containing a photochromic dye.

FIG. 4 illustrates an example of a secondary package 300 in which the tunability of a hair dye composition is depicted as a spectrum 301 of color that can be obtained based on the exposure of the hair dye composition to activating and/or deactivating EMR.

In some aspects, the hair dye product may be provided as a kit that includes two or more photochromic dyes and/or photochromic hair dye compositions that can be combined by a user to form a hair dye mixture that provides a desired hair color. In some aspects, the kit includes two or more hair dye compositions, each comprising a photochromic dye, a suitable solvent, and, optionally, other ingredients commonly included in a hair dye composition. In some aspects, the kit includes two or more photochromic dyes powders that can be combined before or after dissolving the powder in a suitable solvent or carrier. The photochromic hair dye powders and/or hair dye compositions in the kit can be combined at different ratios to provide a variety of different hair colors. The kit may also include a mixing container for combining the photochromic dye powders and/or hair dye compositions. The photochromic dyes may be activated and/or deactivated before and/or after forming a hair dye mixture.

METHODS

Color Measurement

This method enables the measurement of both the initial color and color change on hair treated with the hair dye compositions herein. The method uses a suitable spectrophotometer or colorimeter such as an X-Rite Ci7800 sphere benchtop brand spectrophotometer, Konica Minolta CM-3600A brand spectrometer or equivalent according to the manufacturer's instructions. The value used to express the degree of color change on any particular substrate is Delta E (ΔE), which is calculated using L*, a* and b* values ("Lab values") according to the following equation:

$$\Delta E = \sqrt{((L_1 - L_2)^2 + (a_1 - a_2)^2 + (b_1 - b_2)^2)},$$

where:

$L_1$ is the first L* value and $L_2$ is the second L* value;

$a_1$ is the first a* value and $a_2$ is the second a* value; and $b_1$ is the first b* value and $b_2$ is the second b* value.

L* is a measure of lightness and darkness (color intensity), wherein L=100 is white, and L=0 is black. The a* value is a measure of the red and green quotients (color hues) in which positive values equate to red and negative values equate to green. The b* value is a measure of the yellow and blue quotients (color hues) in which positive values equate to yellow and negative values equate to blue.

The Lab value measurements are carried out on a full scanning spectrophotometer with a wavelength of from 400-700 nanometers. The spectrophotometer is set to: mode=SCI/SCE; spot size=10 mm; and light=D65. The spectrophotometer records the color in terms of L* a* and b* values, which can be converted into other color systems (such as the HSL color system) using known conversion techniques.

When the sample is a hair tress (e.g., standard hair switch), the sample is placed in a holder designed to hold the hair sample in a uniform orientation during measurement and ensure it does not move during measurement. For example, the hair switch may be place on a hard, flat surface (e.g., board) and secured at the top and bottom to prevent movement. In some instances, it may be desirable to comb the hair sample prior to securing it so it lies flat on the surface. The hair should be spread to cover the 10 mm port of the spectrophotometer during color measurement. Three measurements are run per treatment.

EXAMPLES

Example 1: Example Formulations

Table 1 shows hair dye composition formulas that may be suitable for use as hair dye compositions herein.

TABLE 1

| | Product Form | Ingredient list |
|---|---|---|
| Inventive 1 | Oil-based | Isododecane, dimethicone, dimethiconol, diethyl sebacate, isodecyl pivalate, tris(ethylhexanoate) glyceryl, coconut oil, DAE dye, fragrance, phenoxyethanol, tocopherol, jojoba seed oil, |
| Inventive 2 | Water based | Tween80, coconut oil, water, DAE dye, fragrance |
| Inventive 3 | Mousse | Cyclohexasiloxane, dimethicone, dimethicone/vinyl dimethicone crosspolymer, silica, acrylates copolymer, disodium stearoyl glutamate, aluminum hydroxide, coconut oil, DAE dye, fragrance |
| Inventive 4 | Solid powder | Talc, dimethicone, HDI/trimethylol hexyllactone crosspolymer, silica, dimethicone/vinyl dimethicone crosspolymer, mica, titanium dioxide (CI 77891), DAE dye, triethoxycaprylylsilane, ethylhexylglycerin, glyceryl caprylate, dimethiconol, iron oxides (CI 77492), aluminum hydroxide, alcohol, butylene glycol, iron oxides (CI 77491), methicone, tocopherol |
| Inventive 5 | Soft gel | Water, iota carrageenan, tween 80, coconut oil, DAE-dye |

Example 2: Activating EMR and Deactivating EMR for Diarylethene Photochromic Dyes Table 2 shows the activating EMR and deactivating EMR for specific p-type photochromic dyes DAE-0001 (cyan), DAE-0012 (magenta), and DAE-0068 (yellow).

TABLE 2

| Hair dye compound[1] | Activating EMR | De-activating EMR |
|---|---|---|
| DAE-0001 (cyan) | 250-350 nm | 600-700 nm |
| DAE-0012 (magenta) | 250-350 nm | 500-600 nm |
| DAE-0068 (yellow) | 250-350 nm | 400-500 nm |

[1]From Yamada Chemical Company

Example 3: Colors Achieved by Different Dye Combinations

This example demonstrates the ability of a p-type photochromic dye to change color. Each dye composition tested in this example is a 0.5% dye solution in acetone. The solution was placed in a 30 mL clear glass vial (available from Thermofisher) and exposed to activating EMR with a fluence of 12 J/cm$^2$. HSL values were measured according to the Color Measurement method within 1 minute after removing the activating EMR. The resultant colors are provided in Table 3.

TABLE 3

| | Dye Ratio (w/w) | | | Resultant Color | | |
|---|---|---|---|---|---|---|
| Ex. | Cyan[1] | Magenta[2] | Yellow[3] | H (°) | S (%) | L (%) |
| 1 | 1 | 0 | 0 | 55 | 96 | 70 |
| 2 | 0 | 1 | 0 | 339 | 57 | 56 |
| 3 | 0 | 0 | 1 | 229 | 84 | 53 |
| 4 | 0 | 1 | 1 | 26 | 63 | 52 |
| 5 | 1 | 0 | 1 | 220 | 7 | 17 |
| 6 | 1 | 1 | 0 | 240 | 6 | 15 |
| 7 | 1 | 1 | 1 | 350 | 15 | 10 |

[1]DAE-0001 from Yamada Chemical Company
[2]DAE-0012 from Yamada Chemical Company
[3]DAE-0068 from Yamada Chemical Company

Example 4: Hair Color Change I

This example demonstrates the ability of the inventive hair dye composition to change the color of hair when an unactivated hair dye composition is applied to hair and then exposed to an activating EMR. In this example, three test hair switch types: medium blonde (hair color value 2), medium light brown (hair color value 5), and black (hair color value 9) were tested to demonstrate the properties and benefits of the inventive hair dye compositions. Suitable hair switches should weigh approximately 4 g and be about 8 cm long. The hair switch can be made from natural or synthetic hair. An example of a suitable hair switch is a bleached bundle hair tress available from Kerling Group. The hair dye composition used in this example is Composition 6 from Table 3 above.

The initial color of each hair switch is measured according to the Color Measurement method. The hair switch is dyed by hanging it over a suitable container and applying approximately 8 g of the hair dye composition directly to the test hair switch. The hair dye composition is massaged through the hair switch for 1 minute and then left on the hair switch for 30 minutes. The hair switch is then exposed to activating EMR (250-350 nm and a fluence of 12 J/cm$^2$). The HSL values and Gloss value of the dyed hair switch are measured according to the Color Measurement method described above. The results are summarized in Table 4.

TABLE 4

| | Initial color | | | | After dye composition applied and activated | | | |
|---|---|---|---|---|---|---|---|---|
| Hair Color Value | H (°) | S (%) | L (%) | Gloss | H (°) | S (%) | L (%) | Gloss |
| Medium blonde/2 | 38.9 | 19 | 60 | 24 | 249 | 7 | 41 | 16 |
| Medium light brown/5 | 20 | 27 | 35 | 7 | 21 | 20 | 20 | 7 |
| Black/9 | 245 | 9 | 29 | 4 | 226 | 15 | 28 | 5 |

Example 5: Hair Color Change II

This example demonstrates the ability of the hair dye compositions herein to tunably change the color of hair when applied to hair and then exposed to an activating EMR followed by exposure to one or more deactivating EMR.

The top portion of the activated medium-blonde test hair switch from Table 4 above was exposed to a deactivating EMR having a wavelength of 500 to 600 nm and a fluence of 1.2 J/cm$^2$, while the bottom portion of the hair switch was shielded from the applied deactivating EMR. The bottom portion of the activated test hair switch was then exposed to a deactivating EMR of 600-700 nm and a fluence of 1.2 J/cm$^2$, while the top portion was shielded from the applied deactivating EMR. The HSL values of the top and bottom portions of the hair switch were determined according to the Color Measurement method and the ΔE was calculated. The results are summarized in Table 5 below. The ΔE after activation was determined relative to the original hair color, and the ΔE after deactivation was determined relative to the activated hair color.

TABLE 5

| Color Property | After activation at 250-350 nm | After deactivation at 500-600 nm | After deactivation at 600-700 nm |
|---|---|---|---|
| H (°) | 262.6 | 218.8 | 268.5 |
| S(%) | 10.2 | 1.4 | 6 |
| L(%) | 24 | 32.4 | 31.6 |
| Gloss (gloss units) | 10.8 | 10.8 | 16.3 |
| ΔE | 53.0 | 13.5 | 9.3 |

As can be seen in Table 5, activating the hair dye composition provides a first color change, and the deactivating steps provide second and third color changes.

Example 6: Hair Color Change III

This example provides another demonstration of the ability of the hair dye compositions herein to tunably change the color of hair when the dye composition is exposed to an activating EMR followed by exposure to one or more deactivating EMR. In this example, a test hair switch was prepared as described above and dyed with Composition 6 from Table 3. The dyed hair switch was exposed to an activating EMR having a wavelength of 250-350 nm (UV light) and a fluence of 16 J/cm$^2$, followed by exposure to a first deactivating EMR of 600-700 nm (red light) and then a second deactivating EMR of 500-600 nm (green light). The results of the testing are summarized in Table 6 below.

TABLE 6

| Color Property | Original hair color | Hair color after application of hair dye | Hair color after activation at 250-350 nm | Hair color after deactivation at 600-700 nm | Hair Color after deactivation at 500-600 nm |
|---|---|---|---|---|---|
| H (°) | 36 | 38 | 236 | 346 | 240 |
| S(%) | 40 | 40 | 11 | 12 | 1 |
| L(%) | 76 | 73 | 51 | 58 | 68 |

As can be seen in Table 6, even applying unactivated dye resulted in a hair color change. Activation and deactivation of the dye produced 3 additional hair colors.

Example 7: Hair Color Change IV

This example provides another demonstration of the ability of the hair dye compositions herein to tunably change the color of hair when the dye composition is exposed to an activating EMR prior to applying the dye to the hair. Composition 6 from Table 3 (cyan+magenta) was also used in this test. However, the photochromic dyes were activated with an activating EMR (250-350 nm, 12 J/cm$^2$) prior to applying it to the hair. After the activated dye composition was applied to the hair, it was exposed to a deactivating EMR (600-700 nm, 1.2 J/cm$^2$). The results of the testing are summarized in Table 7 below.

TABLE 7

| Color Property | Original hair color | Original hair dye composition color | Hair dye composition color after activation | Hair color after application of dye | Hair color after deactivation |
|---|---|---|---|---|---|
| H (°) | 38 | 46 | 234 | 20 | 25 |
| S(%) | 51 | 34 | 23 | 18 | 27 |
| L(%) | 71 | 80 | 33 | 33 | 42 |

As can be seen in Table 7, activating the dye prior to application to the hair yields a different color versus applying the dye and then activating. Deactivating the dye also produces a different color change relative to dye that is activated after application to the hair. In this example, the hair dye composition may be completely deactivated (i.e., returned to its pre-activated clear and substantially colorless form) and then activated again to produce the color change effect demonstrated in Example 4. Thus, a single hair color composition herein could provide 6 or more different hair colors.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tunable keratin dye composition, comprising:

a first photochromic dye activatable by a first activating electromagnetic radiation (EMR) and deactivatable by a first deactivating EMR;

a second photochromic dye activatable by a second activating EMR and deactivatable by a second deactivating EMR, wherein the first and second deactivating EMR are different; and a third photochromic dye activatable by a third activating EMR and deactivatable by a third deactivating EMR, wherein the first, second, and third deactivating EMR are different;

a carrier.

2. The composition of claim 1, wherein the first, second, and third activating EMR have a wavelength of between about 100 nm and about 400 nm.

3. The composition of claim 2, wherein the first, second, and third deactivating EMR have a wavelength of about 400 nm to about 700 nm.

4. The composition of claim 1, wherein at least one of the photochromic dyes is a p-type photochromic dye.

5. The composition of claim 1, wherein the carrier is selected from an emulsifier, a fatty acid, a fatty alcohol, a fatty ester, a silicone, or a combination of thereof.

6. The composition of claim 5, wherein the carrier is selected from the group consisting of coconut oil, isopropyl palmitate, polysorbate, caprylic/capric triglyceride and combinations thereof.

7. The composition of claim 1, wherein the composition is free of acetone, toluene and formaldehyde.

8. The composition of claim 1, wherein the first and second photochromic dyes are present at a weight ratio of first dye to second dye of between 1:10 and 10:1.

9. The composition of claim 1, wherein the keratin dye composition provides a color change for more than 12 hours.

10. The composition of claim 9, wherein the keratin dye composition provides a color change for more than 24 hours.

* * * * *